United States Patent
Johansen et al.

(10) Patent No.: US 10,953,004 B2
(45) Date of Patent: Mar. 23, 2021

(54) COMBINATION THERAPY FOR PROLIFERATIVE DISEASES

(71) Applicant: Avexxin AS, Trondheim (NO)

(72) Inventors: Berit Johansen, Trondheim (NO); Astrid Jullumstrø Feuerherm, Trondheim (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 16/084,845

(22) PCT Filed: Mar. 14, 2017

(86) PCT No.: PCT/EP2017/056022
§ 371 (c)(1),
(2) Date: Sep. 13, 2018

(87) PCT Pub. No.: WO2017/157955
PCT Pub. Date: Sep. 21, 2017

(65) Prior Publication Data
US 2019/0076423 A1    Mar. 14, 2019

(30) Foreign Application Priority Data

Mar. 14, 2016  (GB) .................................... 1604316

(51) Int. Cl.
*A61K 31/121* (2006.01)
*A61K 31/4745* (2006.01)
(Continued)

(52) U.S. Cl.
CPC ........ *A61K 31/4745* (2013.01); *A61K 9/0019* (2013.01); *A61K 31/121* (2013.01); *A61P 35/00* (2018.01)

(58) Field of Classification Search
CPC .... A61K 31/121; A61K 31/4745; A61P 35/00
(Continued)

(56) References Cited

U.S. PATENT DOCUMENTS 4,649,215 A   3/1987  von Sprecher et al.
4,670,465 A   6/1987  Guzman et al.
(Continued)

FOREIGN PATENT DOCUMENTS

AU   2008200812 A1   3/2008
CN      1678323 A   10/2005
(Continued)

OTHER PUBLICATIONS

U.S. Appl. No. 10/502,414, filed Jan. 11, 2005, U.S. Pat. No. 7,687,543.
(Continued)

*Primary Examiner* — Craig D Ricci
*Assistant Examiner* — Janet L. Coppins
(74) *Attorney, Agent, or Firm* — McCarter & English, LLP; Steven G. Davis

(57) ABSTRACT

A combination product comprising: (A) a compound of formula (I) R-L-CO—X (I) wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds; L is a linking group forming a bridge of 1 to 5 atoms between the R group and the carbonyl CO wherein L comprises at least one heteroatom in the backbone of the linking group; and X is an electron withdrawing group; or a salt thereof; and (B) a compound of formula (X) where $R_1$ is phenyl wherein said phenyl is substituted by lower alkyl unsubstituted or substituted by cyano; $R_3$ is lower alkyl, such as methyl; and $R_4$ is quinolinyl unsubstituted or substituted by halogen; or a tautomer thereof, or a pharmaceutically acceptable salt, or a hydrate or solvate thereof.

(Continued)

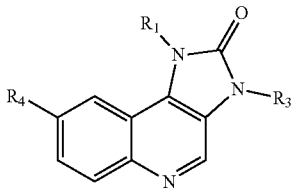

6 Claims, 1 Drawing Sheet

(51) Int. Cl.
*A61K 9/00* (2006.01)
*A61P 35/00* (2006.01)
(58) Field of Classification Search
USPC .................................................. 514/293
See application file for complete search history.

(56) References Cited

U.S. PATENT DOCUMENTS

| | | | |
|---|---|---|---|
| 6,255,496 B1 | 7/2001 | Banville et al. | |
| 6,688,468 B2 | 2/2004 | Waterman | |
| 7,101,875 B2 | 9/2006 | McKew et al. | |
| 7,667,039 B2 * | 2/2010 | Garcia-Echeverria | ................... A61P 27/02 546/82 |
| 7,687,543 B2 | 3/2010 | Johansen et al. | |
| 8,524,776 B2 | 9/2013 | Johansen et al. | |
| 8,796,251 B2 | 8/2014 | Johansen et al. | |
| 8,865,768 B2 | 10/2014 | Johansen et al. | |
| 9,187,396 B2 | 11/2015 | Johansen et al. | |
| 9,375,409 B2 | 6/2016 | Johansen et al. | |
| 9,682,930 B2 | 6/2017 | Feuerherm et al. | |
| 10,085,952 B2 | 10/2018 | Johansen | |
| 10,085,953 B2 | 10/2018 | Johansen et al. | |
| 2005/0165116 A1 | 7/2005 | Johansen et al. | |
| 2005/0256141 A1 | 11/2005 | Nakagawa et al. | |
| 2005/0281755 A1 | 12/2005 | Zarif et al. | |
| 2005/0282792 A1 | 12/2005 | Andres | |
| 2006/0162240 A1 | 7/2006 | Filippini et al. | |
| 2008/0300229 A1 | 12/2008 | Willcox et al. | |
| 2009/0192201 A1 | 7/2009 | Selman-Housein Sosa | |
| 2010/0080768 A1 | 4/2010 | McGraw et al. | |
| 2010/0204298 A1 | 8/2010 | Levy | |
| 2010/0311843 A1 | 12/2010 | Johansen et al. | |
| 2011/0053898 A1 | 3/2011 | Mehta et al. | |
| 2015/0066474 A1 | 3/2015 | Yi et al. | |
| 2015/0258119 A1 | 9/2015 | Kandavalli et al. | |
| 2019/0167606 A1 | 6/2019 | Johansen | |
| 2019/0209585 A1 | 7/2019 | Johansen et al. | |
| 2019/0216815 A1 | 7/2019 | Johansen et al. | |

FOREIGN PATENT DOCUMENTS

| | | | |
|---|---|---|---|
| CN | 103127140 A | 6/2013 | |
| CN | 103249408 A | 8/2013 | |
| CN | 104968349 A | 10/2015 | |
| EP | 0418680 A2 | 3/1991 | |
| EP | 0765661 A2 | 4/1997 | |
| EP | 1970049 A1 | 9/2008 | |
| EP | 2147910 A1 | 1/2010 | |
| EP | 2839833 A1 | 2/2015 | |
| JP | H-08-109128 A | 4/1996 | |
| JP | H09-143067 A | 6/1997 | |
| JP | 09-268153 | 10/1997 | |
| JP | H11-199493 A | 7/1999 | |
| JP | 2000-095683 A | 4/2000 | |
| JP | 2000-508645 A | 7/2000 | |
| JP | 2005-518419 A | 6/2005 | |
| JP | 2009-62316 A | 3/2009 | |
| JP | 2012-528813 A | 11/2012 | |
| JP | 2013-540713 A | 11/2013 | |
| WO | WO-1997/38688 A1 | 10/1997 | |
| WO | WO-1997/44026 A1 | 11/1997 | |
| WO | WO-1999/042101 A1 | 8/1999 | |
| WO | WO-2000/02561 A1 | 1/2000 | |
| WO | WO-2000/034348 A1 | 6/2000 | |
| WO | WO-2001/05761 A1 | 1/2001 | |
| WO | WO-2002/060535 A1 | 8/2002 | |
| WO | WO-2003/063878 A1 | 8/2003 | |
| WO | WO-2003/101487 A1 | 12/2003 | |
| WO | WO-2004/064715 A2 | 8/2004 | |
| WO | WO-2004/082402 A1 | 9/2004 | |
| WO | WO-2005/123060 A1 | 12/2005 | |
| WO | WO-2005/123061 A1 | 12/2005 | |
| WO | WO-2006/096579 A1 | 9/2006 | |
| WO | WO-2006/106438 A2 | 10/2006 | |
| WO | WO-2006/122806 A2 | 11/2006 | |
| WO | WO-2007/075841 A1 | 7/2007 | |
| WO | WO-2007/135518 A2 | 11/2007 | |
| WO | WO-2008/070129 A2 | 6/2008 | |
| WO | WO-2008/075366 A2 | 6/2008 | |
| WO | WO-2008/075978 A2 | 6/2008 | |
| WO | WO-2008/110815 A1 | 9/2008 | |
| WO | WO-2009/038671 A2 | 3/2009 | |
| WO | WO-2009/061208 A1 | 5/2009 | |
| WO | WO-2010/125340 A1 | 11/2010 | |
| WO | WO-2010/128401 A1 | 11/2010 | |
| WO | WO-2010/139482 A1 | 12/2010 | |
| WO | WO-2011/039365 A1 | 4/2011 | |
| WO | WO-2011/097276 A1 | 8/2011 | |
| WO | WO-2011/154004 A1 | 12/2011 | |
| WO | WO-2012/02688 A2 | 1/2012 | |
| WO | WO-2012/013331 A2 | 2/2012 | |
| WO | WO-2012/028688 A1 | 3/2012 | |
| WO | WO-2013/150386 A2 | 10/2013 | |
| WO | WO-2014/019841 A1 | 2/2014 | |
| WO | WO-2014/082960 A1 | 6/2014 | |
| WO | WO-2014/132134 A1 | 9/2014 | |
| WO | WO-2014/142995 A1 | 9/2014 | |
| WO | WO-2015/181135 A1 | 12/2015 | |
| WO | WO-2015181135 A1 * | 12/2015 | ........... A61K 31/121 |

OTHER PUBLICATIONS

U.S. Appl. No. 12/713,917, filed Feb. 26, 2010, U.S. Pat. No. 8,524,776.
U.S. Appl. No. 13/957,899, filed Aug. 2, 2013, U.S. Pat. No. 8,865,768.
U.S. Appl. No. 14/487,382, filed Sep. 16, 2014, U.S. Pat. No. 9,375,409.
U.S. Appl. No. 15/166,121, filed May 26, 2016.
U.S. Appl. No. 15/404,536, filed Jan. 12, 2017.
U.S. Appl. No. 15/686,378, filed Aug. 25, 2017.
U.S. Appl. No. 15/907,969, filed Feb. 28, 2018.
U.S. Appl. No. 16/171,925, filed Oct. 26, 2018.
U.S. Appl. No. 16/436,419, filed Jun. 10, 2019.
U.S. Appl. No. 12/794,367, filed Jun. 4, 2010, U.S. Pat. No. 8,796,251.
U.S. Appl. No. 14/200,238, filed Mar. 7, 2014, U.S. Pat. No. 9,187,396.
U.S. Appl. No. 13/783,088, filed Mar. 1, 2013, U.S. Pat. No. 9,682,930.
U.S. Appl. No. 15/623,962, filed Jun. 15, 2017.
U.S. Appl. No. 14/647,765, filed May 27, 2015, U.S. Pat. No. 10,085,952.
U.S. Appl. No. 16/117,148, filed Aug. 30, 2018, 2019-0167606.
U.S. Appl. No. 15/360,084, filed Nov. 23, 2016, U.S. Pat. No. 10,085,953.
U.S. Appl. No. 16/117,175, filed Aug. 30, 2018.
U.S. Appl. No. 16/389,453, filed Apr. 19, 2019.
U.S. Appl. No. 16/306,126, filed Nov. 30, 2018.
U.S. Appl. No. 16/306,106, filed Nov. 30, 2018, 2019-0209585.

(56) References Cited

OTHER PUBLICATIONS

U.S. Appl. No. 16/306,161, filed Nov. 30, 2018.
U.S. Appl. No. 16/306,092, filed Nov. 30, 2018, 2019-0216815.
U.S. Appl. No. 16/334,835, filed Mar. 20, 2019.
U.S. Appl. No. 16/334,916, filed Mar. 20, 2019.
Albanesi. Keratinocytes in allergic skin diseases. Curr Opin Allergy Clin Immunol. Oct. 2010;10(5):452-6.
Albrightson et al., Selective inhibition of 5-lipoxygenase attenuates glomerulonephritis in the rat. Kidney Int. May 1994;45(5):1301-10.
Aldámiz-Echevarría et al., Effect of docosahexaenoic acid administration on plasma lipid profile and metabolic parameters of children with methylmalonic acidaemia. J Inherit Metab Dis. Feb. 2006;29(1):58-63.
Alexander et al., Arachidonic acid induces ERK activation via Src SH2 domain association with the epidermal growth factor receptor. Kidney Int. May 2006;69(10):1823-32.
Allen et al., Systemic exposure, tolerability, and efficacy of pimecrolimus cream 1% in atopic dermatitis patients. Arch Dis Child. Nov. 2003;88(11):969-73.
Andersen et al., Elevated expression of human nonpancreatic phospholipase A2 in psoriatic tissue. Inflammation. Feb. 1994;18(1):1-12.
Anthonsen et al., Functional coupling between secretory and cytosolic phospholipase A2 modulates tumor necrosis factor-alpha-and interleukin-1beta-induced NF-kappa B activation. J Biol Chem. Aug. 10, 2001;276(32):30527-36.
Atsumi et al., Distinct roles of two intracellular phospholipase A2s in fatty acid release in the cell death pathway. Proteolytic fragment of type IVA cytosolic phospholipase A2alpha inhibits stimulus-induced arachidonate release, whereas that of type VI Ca2+-independent phospholipase A2 augments spontaneous fatty acid release. J Biol Chem. Jun. 16, 2000;275(24):18248-58.
Blauvelt et al., 11. Allergic and immunologic diseases of the skin. J Allergy Clin Immunol. Feb. 2003;111(2 Suppl):S560-70.
British Association of Dermatologists, Methotrexate. Retrieved online at: http://www.bad.org.uk/for-the-public/patient-information-leaflets/methotrexate. 5 pages, (2015).
Brown et al., Protection of oxygen-sensitive pharmaceuticals with nitrogen. J Pharm Sci. Feb. 1969;58(2):242-5.
Cannon, Analog Design. Burger's Medicinal Chemistry and Drug Discovery. Fifth Edition, vol. I: Principles and Practice. Manfred E. Wolff (Ed.), John Wiley & Sons, Inc., New York. Chapter 19, pp. 783-802, (1995).
Cattell et al., Nitric oxide and glomerulonephritis. Kidney Int. Mar. 2002;61(3):816-21.
Chadban et al., Glomerulonephritis. Lancet. May 21-27, 2005;365(9473):1797-806.
Chen, Potential value and limitation of dual inhibitors of PI3K and mTOR in the treatment of cancer. Curr Cancer Drug Targets. Feb. 2013;13(2):117-20.
Costabile et al., The immunomodulatory effects of novel beta-oxa, beta-thia, and gamma-thia polyunsaturated fatty acids on human T lymphocyte proliferation, cytokine production, and activation of protein kinase C and MAPKs. J Immunol. Jan. 1, 2005;174(1):233-43.
Couser et al., Pathogenesis of glomerular damage in glomerulonephritis. Nephrol Dial Transplant. 1998;13 Suppl 1:10-5.
Cybulsky et al., Complement C5b-9 membrane attack complex increases expression of endoplasmic reticulum stress proteins in glomerular epithelial cells. J Biol Chem. Nov. 1, 2002;277(44):41342-51.
Cybulsky et al., Complement-induced phospholipase A2 activation in experimental membranous nephropathy. Kidney Int. Mar. 2000;57(3):1052-62.
Edmundson et al., Treatment of psoriasis with folic acid antagonists. AMA Arch Derm. Aug. 1958;78(2):200-3.
Edwards et al., Omega-3 Fatty Acids and PPARgamma in Cancer. PPAR Res. 2008;2008:358052. 14 pages.
Everyscience, Glossary-E. everyscience.com. 3 pages, (2004).
Flock et al., Syntheses of some polyunsaturated sulfur-and oxygen-containing fatty acids related to eicosapentaenoic and docosahexaenoic acids. Acta Chem Scand. Jun. 1999;53(6):436-45.
Flock et al., Syntheses of Some Sulfur-Containing Polyunsaturated Fatty Acids as Potential Lipoxygenase Inhibitors. Synthetic Communications. 2007;37(22):4005-4015.
Gautam et al., Identification of selective cytotoxic and synthetic lethal drug responses in triple negative breast cancer cells. Mol Cancer. May 10, 2016;15(1):34. 16 pages.
Gutfreund et al., Topical calcineurin inhibitors in dermatology. Part I: Properties, method and effectiveness of drug use. Postepy Dermatol Alergol. Jun. 2013;30(3):165-9.
Hagiwara et al., Eicosapentaenoic acid ameliorates diabetic nephropathy of type 2 diabetic KKAy/Ta mice: involvement of MCP-1 suppression and decreased ERK1/2 and p38 phosphorylation. Nephrol Dial Transplant. Mar. 2006;21(3):605-15.
Hansen et al., Syntheses of two cytotoxic polyunsaturated pyrrole metabolites of the marine sponge Mycale micracanthoxea. Tetrahedron Letters. Mar. 22, 2004;45(13):2809-2811.
Hao et al., Roles of lipid mediators in kidney injury. Semin Nephrol. May 2007;27(3):338-51.
Holmeide et al., Syntheses of some polyunsaturated trifluoromethyl ketones as potential phospholipase A2 inhibitors. J Chem Soc, Perkin Trans 1. 2000;1:2271-6.
Hua et al., AKT and cytosolic phospholipase A2a form a positive loop in prostate cancer cells. Curr Cancer Drug Targets. 2015;15(9):781-91.
Huber et al., Synovial fibroblasts: key players in rheumatoid arthritis. Rheumatology (Oxford). Jun. 2006;45(6):669-75.
Huwiler et al., The Omega3-polyunsaturated fatty acid derivatives AVX001 and AVX002 directly inhibit cytosolic phospholipase A(2) and suppress PGE(2) formation in mesangial cells. Br J Pharmacol. Dec. 2012;167(8):1691-701.
Ingber et al., A novel treatment of contact dermatitis by topical application of phospholipase A2 inhibitor: a double-blind placebo-controlled pilot study. Int J Immunopathol Pharmacol. Jan.-Mar. 2007;20(1):191-5.
Johannesdottir et al., Nonsteroidal anti-inflammatory drugs and the risk of skin cancer: a population-based case-control study. Cancer. Oct. 1, 2012;118(19):4768-76.
Johansen et al., Novel inhibitors of cytosolic Group IVA phospholipase A2 (cPLA2) ameliorate collagen induced arthritis. Br J Pharmacol. 2012;167:1691, Abstract No. 25.
Johansen et al., Phospholipase A2 in Psoriasis. Basic and Clinical Aspects in Inflammatory Diseases. Prog Surg. 1997;24:225-31.
Katagiri et al., Trifluoromethylated amino alcohol as chiral auxiliary for highly diastereoselective and fast Simmons-Smith cyclopropanation of allylic amine. Tetrahedron: Asymmetry. Apr. 18, 2006;17(8):1157-1160.
Kishida et al., Distinctive inhibitory activity of docosahexaenoic acid against sphingosine-induced apoptosis. Biochim Biophys Acta. Apr. 22, 1998;1391(3):401-8.
Kurogi, Mesangial cell proliferation inhibitors for the treatment of proliferative glomerular disease. Med Res Rev. Jan. 2003;23(1):15-31.
Kusunoki et al., Pro-apoptotic effect of nonsteroidal anti-inflammatory drugs on synovial fibroblasts. Mod Rheumatol. 2008;18(6):542-51.
Lamothe et al., Efficacy of giripladib, a novel inhibitor of cytosolic phospholipase A2alpha, in two different mouse models of rheumatoid arthritis. Clin Immunol. 2008;127:S89-90. Abstract Sa.29.
Larsen et al., Polyunsaturated thia-and oxa-fatty acids: incorporation into cell-lipids and their effects on arachidonic acid-and eicosanoid synthesis. Biochim Biophys Acta. Oct. 18, 1997;1348(3):346-54.
Lianos et al., Biosynthesis and role of arachidonic acid metabolites in glomerulonephritis. Nephron. 1984;37(2):73-7.
Liu et al., EGFR signaling is required for TGF-beta 1 mediated COX-2 induction in human bronchial epithelial cells. Am J Respir Cell Mol Biol. Nov. 2007;37(5):578-88.
Ma et al., 12/15-lipoxygenase inhibitors in diabetic nephropathy in the rat. Prostaglandins Leukot Essent Fatty Acids. Jan. 2005;72(1):13-20.

(56) References Cited

OTHER PUBLICATIONS

Maira et al., Identification and characterization of NVP-BEZ235, a new orally available dual phosphatidylinositol 3-kinase/mammalian target of rapamycin inhibitor with potent in vivo antitumor activity. Mol Cancer Ther. Jul. 2008;7(7):1851-63.
Malaviya et al., Targeting cytosolic phospholipase A2 by arachidonyl trifluoromethyl ketone prevents chronic inflammation in mice. Eur J Pharmacal. Jun. 13, 2006;539(3):195-204.
Matsuzawa et al., Activation of cytosolic phospholipase A2alpha by epidermal growth factor (EGF) and phorbol ester in HeLa cells: different effects of inhibitors for EGF receptor, protein kinase C, Src, and C-Raf. J Pharmacol Sci. Oct. 2009;111(2):182-92.
McKew et al., Indole cytosolic phospholipase A2 alpha inhibitors: discovery and in vitro and in vivo characterization of 4-{3-[5-chloro-2-(2-{[(3,4-dichlorobenzyl)sulfonyl]amino}ethyl)-1-(diphenylmethyl)-1H-indol-3-yl]propyl}benzoic acid, efipladib. J Med Chem. Jun. 26, 2008;51(12):3388-413.
Miller et al., Dietary supplementation with ethyl ester concentrates of fish oil (n-3) and borage oil (n-6) polyunsaturated fatty acids Induces epidermal generation of local putative anti-inflammatory metabolites. J Invest Dermatol. Jan. 1991;96(1):98-103.
Mizoguchi et al., Cyclosporin ointment for psoriasis and atopic dermatitis. Lancet. May 2, 1992;339(8801):1120.
Nakamura et al., Effects of eicosapentaenoic acids on oxidative stress and plasma fatty acid composition in patients with lupus nephritis. In Vivo. Sep.-Oct. 2005;19(5):879-82.
Ono et al., Characterization of a novel inhibitor of cytosolic phospholipase A2alpha, pyrrophenone. Biochem J. May 1, 2002;363(Pt 3):727-35.
Papanikolaou, Alteration of mercuric chloride-induced autoimmune glomerulonephritis in brown-Norway rats by herring oil, evening primrose oil and OKY-046 a selective TXA-synthetase inhibitor. Prostaglandins Leukot Med. May 1987;27(2-3):129-49.
Proudman et al., Fish oil in recent onset rheumatoid arthritis: a randomised, double-blind controlled trial within algorithm-based drug use. Ann Rheum Dis. Jan. 2015;74(1):89-95.
Ringbom et al., Cox-2 inhibitory effects of naturally occurring and modified fatty acids. J Nat Prod. Jun. 2001;64(6):745-9.
Robinson et al., Suppression of autoimmune disease by dietary n-3 fatty acids. J Lipid Res. Aug. 1993;34(8):1435-44.
Rodriguez et al., Hyperosmotic stress induces phosphorylation of cytosolic phospholipase A(2) in HaCaT cells by an epidermal growth factor receptor-mediated process. Cell Signal. Oct. 2002;14(10):839-48.
Ryan et al., The Treatment of Psoriasis With Folic Acid Antagonists. Br J Dermatol. Dec. 1964;76:555-64.
Sakaguchi et al., Truncation of annexin A1 is a regulatory lever for linking epidermal growth factor signaling with cytosolic phospholipase A2 in normal and malignant squamous epithelial cells. J Biol Chem. Dec. 7, 2007;282(49):35679-86.
Sandri et al., Syntheses of all-(Z)-5,8,11,14,17-Eicosapentaenoic Acid and all-(Z)-4,7,10,13,16,19-Docosahexaenoic Acid from (Z)-1,1,6,6-tetraisopropoxy-3-hexene. J Org Chem. 1995;60(20):6627-30.
Schalkwijk et al., Maximal epidermal growth-factor-induced cytosolic phospholipase A2 activation in vivo requires phosphorylation followed by an increased intracellular calcium concentration. Biochem J. Jan. 1, 1996;313 ( Pt 1):91-6.
Scheinfeld, The use of topical tacrolimus and pimecrolimus to treat psoriasis: a review. Dermatol Online J. Jul. 15, 2004;10(1):3. 5 pages.
Scuderi et al., Expression of Ca(2+)-independent and Ca(2+)-dependent phospholipases A(2) and cyclooxygenases in human melanocytes and malignant melanoma cell lines. Biochim Biophys Acta. Oct. 2008;1781(10):635-42.
Sene et al., Silicones as Excipients for Topical Pharmaceutical Applications. The Silky Touch Product Family from Dow Corning. Dow Corning Corporation, retrieved online at: www.dowcorning.co.jp/ja_JP/content/published.lit/52/1034-01.pdf. 12 pages (2002).

Sheridan, The most common chemical replacements in drug-like compounds. J Chem Inf Comput Sci. Jan.-Feb. 2002;42(1):103-8.
Shi et al., Attenuation of mycotoxin-induced IgA nephropathy by eicosapentaenoic acid in the mouse: dose response and relation to IL-6 expression. J Nutr Biochem. Oct. 2006;17(10):697-706.
Six et al., Structure-activity relationship of 2-oxoamide inhibition of group IVA cytosolic phospholipase A2 and group V secreted phospholipase A2. J Med Chem. Aug. 23, 2007;50(17):4222-35.
Six et al., The expanding superfamily of phospholipase A(2) enzymes: classification and characterization. Biochim Biophys Acta. Oct. 31, 2000;1488(1-2):1-19.
Sjursen et al., Secretory and cytosolic phospholipase A(2)regulate the long-term cytokine-induced eicosanoid production in human keratinocytes. Cytokine. Aug. 2000;12(8):1189-94.
Sommerfelt et al., Cytosolic phospholipase A2 regulates TNF-induced production of joint destructive effectors in synoviocytes. PLoS One. Dec. 12, 2013;8(12):e83555. 8 pages.
Stewart, Calcipotriol for psoriasis, Dovonex. Patient, retrieved online at: https:patient.info/medicine/calcipotriol-for-psoriasis-dovonex. 3 pages, (2015).
Stewart. Tacalcitol for psoriasis, Curatoderm. Patient, retrieved online at: https://patient.info/medicine/tacalcitol-for-psoriasis-curatoderm. 6 pages, (2015).
Sundler et al., Acyl-chain selectivity of the 85 kDa phospholipase A2 and of the release process in intact macrophages. Biochem J. Jul. 15, 1994;301 ( Pt 2):455-8.
Tai et al., Cytosolic phospholipase A2 alpha inhibitor, pyrroxyphene, displays anti-arthritic and anti-bone destructive action in a murine arthritis model. Inflamm Res. Jan. 2010;59(1):53-62.
Thommesen et al., Selective inhibitors of cytosolic or secretory phospholipase A2 block TNF-induced activation of transcription factor nuclear factor-kappa B and expression of ICAM-1. J Immunol. Oct. 1, 1998 ;161(7):3421-30.
WebMD, Sking Problems & Treatments Health Center, Psoriasis Overview. Retrieved online at: http://www.webmd.com/skin-problems-and-treatments/psoriasis-overview. 2 pages, Sep. 1, 2005.
Wen et al., Critical role of arachidonic acid-activated mTOR signaling in breast carcinogenesis and angiogenesis. Oncogene. Jan. 10, 2013;32(2):160-70.
Yan et al., Cytosolic Phospholipase A2 is Involved in Epidermal Growth Factor and Fetal Bovine Serum-induced Proliferation in Hela Cells. Chinese Doctoral Dissertation & Master's Theses. 68 pages. (2005).
Zulfakar et al., Enhanced topical delivery and ex vivo anti-inflammatory activity from a betamethasone dipropionate formulation containing fish oil. Inflamm Res. Jan. 2010;59(1):23-30.
European Office Action for Application No. 11757227.1, dated Mar. 19, 2014. 8 pages.
International Search Report and Written Opinion for Application No. PCT/EP2010/003384, dated Aug. 6, 2010.
International Search Report and Written Opinion for Application No. PCT/EP2011/065123, dated Dec. 23, 2011. 14 pages.
International Search Report and Written Opinion for Application No. PCT/EP2013/074612, dated Mar. 18, 2014.
International Search Report and Written Opinion for Application No. PCT/EP2017/056022, dated Jul. 5, 2017. 17 pages.
International Search Report and Written Opinion for Application No. PCT/EP2017/063625, dated Sep. 8, 2017, 11 pages.
International Search Report and Written Opinion for Application No. PCT/EP2017/063627, dated Sep. 8, 2017, 11 pages.
International Search Report and Written Opinion for Application No. PCT/EP2017/063628, dated Sep. 8, 2017, 12 pages.
International Search Report and Written Opinion for Application No. PCT/EP2017/063629, dated Sep. 8, 2017, 12 pages.
International Search Report and Written Opinion for Application No. PCT/EP2017/073951, dated Nov. 13, 2017, 13 pages.
International Search Report and Written Opinion for Application No. PCT/EP2017/073958, dated Dec. 5, 2017, 16 pages.
Japanese Office Action for Application No. 2015-543453, dated Jul. 13, 2017, 5 pages. English translation only.

* cited by examiner

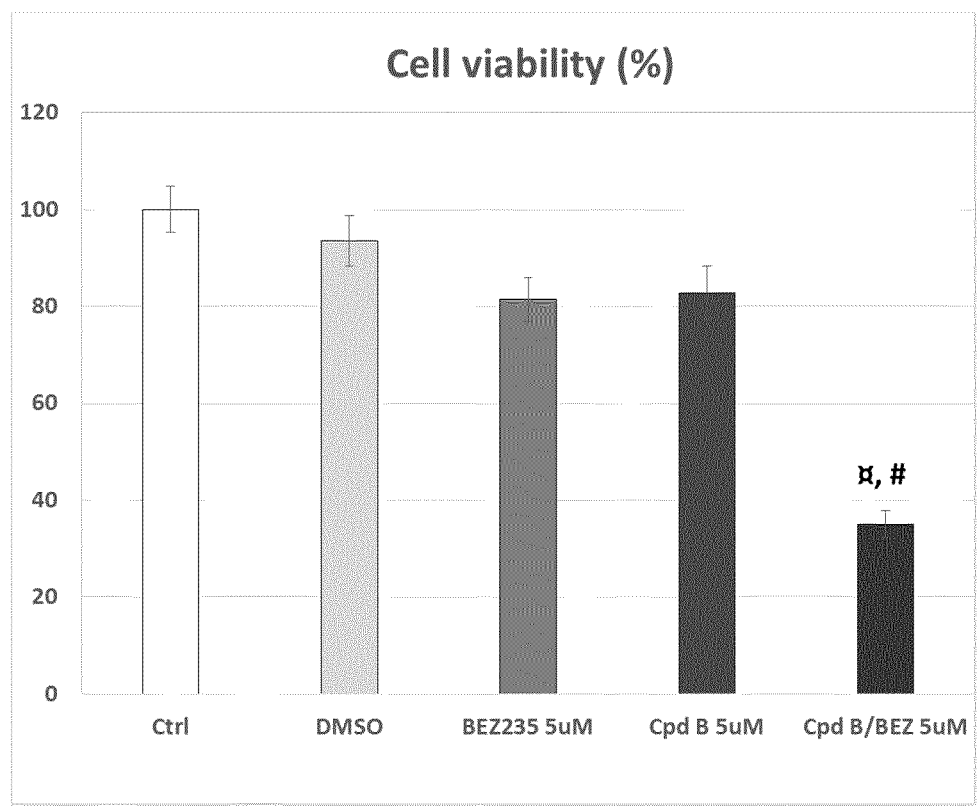

COMBINATION THERAPY FOR PROLIFERATIVE DISEASES

CROSS-REFERENCE TO RELATED APPLICATIONS

This application is a 35 U.S.C. § 371 national stage application of International Application No. PCT/EP2017/056022, filed Mar. 14, 2017, which claims priority to United Kingdom Patent Application No. 1604316.8, filed Mar. 14, 2016.

This invention relates to a pharmaceutical composition or combination product comprising certain polyunsaturated long-chain ketones in combination with certain protein kinase inhibitors, in particular phosphatidylinositol-4,5-bisphosphate 3-kinase inhibitors (PI3K) and more particularly dual inhibitors of PI3K and mammalian target of rapamycin (mTOR). The invention also relates to the use of said pharmaceutical composition or combination product for the treatment or prevention of proliferative conditions such as cancer, e.g. breast cancer. The invention also relates to methods of treating or preventing proliferative conditions in patients comprising administration of the pharmaceutical composition or combination product of the invention to the patient.

BACKGROUND

Basal-like breast cancer (BLBC), which represents ~15% of all breast cancers, is an aggressive molecular subtype of the disease associated with poor prognosis. Most BLBCs are triple-negative (lacking expression of estrogen receptor, progesterone receptor, and human epidermal growth factor receptor 2) and thus unresponsive to currently available targeted therapies. Hence, new molecular targets for treatment are called for.

The present inventors have devised a new combination therapy that targets proliferative conditions in general and breast cancer in particular.

The invention relies on the combination of a long chain polyunsaturated ketone compound and a specific dual inhibitor of PI3K and mTOR. The present inventors have surprisingly found that the combination of these two compounds leads to a combination therapy that works synergistically. In particular, the combination has been shown to synergistically reduce breast cancer cell viability.

SUMMARY OF INVENTION

Thus, viewed from one aspect the invention provides a pharmaceutical composition comprising:

(A) a compound of formula (I):

R-L-CO—X  (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group;

or a salt thereof; and (B) a compound of formula (X)

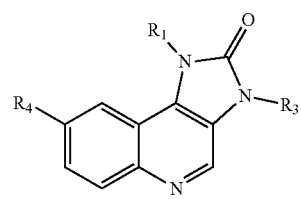

where $R_1$ is phenyl wherein said phenyl is substituted by lower alkyl unsubstituted or substituted by cyano;

$R_3$ is lower alkyl, such as methyl; and $R_4$ is quinolinyl unsubstituted or substituted by halogen;

or a tautomer thereof, or a pharmaceutically acceptable salt, or a hydrate or solvate thereof.

Viewed from another aspect the invention provides a combination product for simultaneous, sequential or separate use comprising:

(A) a compound of formula (I):

R-L-CO—X  (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group;

or a salt thereof; and (B) a compound of formula (X)

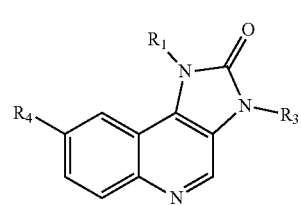

where $R_1$ is phenyl wherein said phenyl is substituted by lower alkyl unsubstituted or substituted by cyano;

$R_3$ is lower alkyl, such as methyl; and $R_4$ is quinolinyl unsubstituted or substituted by halogen;

or a tautomer thereof, or a pharmaceutically acceptable salt, or a hydrate or solvate thereof.

Viewed from another aspect the invention provides a pharmaceutical kit composition for simultaneous, sequential or separate use comprising a first composition comprising a compound (I) as herein defined and a pharmaceutically-acceptable diluent or carrier, and a second composition comprising a compound (X) as herein defined and a pharmaceutically-acceptable diluent or carrier.

In particular, the invention relates to a pharmaceutical composition, combination product or kit as herein before defined in which the compound of formula (I) is:

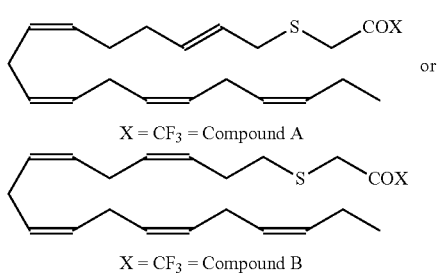

X = CF₃ = Compound A

X = CF₃ = Compound B or a salt thereof; and
the compound of formula (X) is

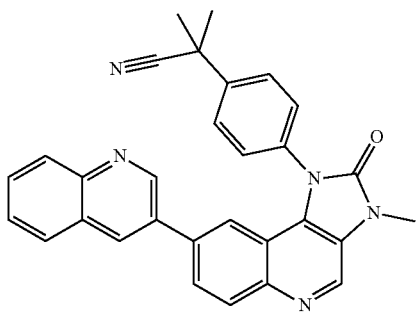 [SMILES: Cn1c(=O)n(-c2ccc(C(C)(C)C#N)cc2)c2c3cc(-c4cnc5ccccc5c4)ccc3ncc21]

or a salt thereof.

Viewed from another aspect the invention provides a pharmaceutical composition or combination product as hereinbefore defined for use in the treatment or prevention of a proliferative disorder such as cancer, especially breast carcinoma.

Viewed from another aspect the invention provides a method of treating or preventing a proliferative disorder such as cancer, especially breast carcinoma in a patient in need thereof comprising administering to said patient, preferably a human, an effective amount of a composition or combination product as herein before defined.

Viewed from another aspect the invention provides a method of treating, such as reducing symptoms of, or preventing a proliferative disorder such as cancer, especially breast carcinoma in a patient in need thereof comprising administering to said patient, preferably a human, an effective amount of a compound of formula (I) and simultaneously, separately or sequentially administering to said patient a compound of formula (X) as herein before defined. In sequential administration either compound can be administered first.

Viewed from another aspect the invention provides a method of treating, such as reducing symptoms of, or preventing a proliferative disorder such as cancer, especially breast carcinoma, in a patient in need thereof comprising:
(i) identifying a patient who has received either a compound of formula (I) or a compound of formula (X) as herein before defined respectively;
(ii) administering to said patient an effective amount of either a compound of formula (X) or a compound of formula (I) as herein before defined so that said patient is administered with both a compound of formula (I) and a compound of formula (X).

Viewed from another aspect the invention provides use of a composition or combination product as hereinbefore defined in the manufacture of a medicament for treating or preventing a proliferative disorder such as cancer, especially breast carcinoma.

Viewed from another aspect the invention provides a process for the preparation of a composition as hereinbefore defined comprising blending a compound of formula (I) and a compound of formula (X) in the presence of at least one pharmaceutical excipient.

Definitions

The term lower alkyl is used herein to refer to C1-6 alkyl groups, preferably C1-4 alkyl groups, especially C1-3 alkyl groups. These alkyl groups can be linear or branched, preferably linear.

The invention relates both to a pharmaceutical composition in which compounds (I) and (X) are blended together in a single composition and to a combination product such as a kit in which the active compounds are provided in separate compositions but are designed for administration simultaneously, separately or sequentially. Any method for treating or preventing a proliferative disorder as defined herein encompasses simultaneous, separate or sequential administration of the active components or administration of the composition of the invention.

A "combination" according to the invention refers to either a fixed combination in one dosage unit form, or a kit of parts for the combined administration where a compound of the formula (I) and its combination partner formula (X)(also referred to as "combination partner" or "therapeutic agent") may be administered independently at the same time or separately within time intervals, especially where these time intervals allow that the combination partners show a cooperative and preferably a synergistic effect.

A "combination product" as used herein means a product suitable for pharmaceutical use that results from the mixing or combining of more than one active ingredient and includes both fixed and non-fixed combinations of the active ingredients. The term "fixed combination" or "fixed dose" means that the active ingredients, e.g. a compound of formula (I) and its combination partner formula (X), are both administered to a patient simultaneously in the form of a single entity or dosage. The term "non-fixed combination" means that the active ingredients, e.g. a compound of formula (I) and the combination partner formula (X) are both administered to a patient as separate entities either simultaneously, concurrently or sequentially with no specific time limits, wherein such administration provides therapeutically effective levels of the two compounds in the body of the warm-blooded animal in need thereof.

All discussion below relating to preferred compounds of the invention is equally applicable to both these aspects of the invention.

DETAILED DESCRIPTION

This invention concerns a combination therapy of a compound of formula (I) and a compound of formula (X). We have surprisingly found that this combination therapy results in synergy. Our results demonstrate a reduction in the viability of breast cancer cells, the composition or combination product offering a larger reduction than could have been expected from the use of individual compounds individually, i.e. the combination of the compounds produces an overall effect that is greater than the sum of the individual elements.

Proliferative Disorder

This invention relates to a new combination therapy for proliferative disorders. Preferably, the composition of the invention is used for the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer.

It is especially preferred if the proliferative disorder is a mammary carcinoma. The composition or combination product of the invention can target specifically metatstaic breast adenocarcinoma.

Composition or Combination Product of the Invention

The invention relies on the therapeutic combination of a compound of formula (I) and a compound of formula (X). The compound of formula (I) is

R-L-CO—X  (I)

wherein R is a $C_{10\text{-}24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group; or a salt thereof.

The group R preferably comprises 5 to 9 double bonds, preferably 5 or 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 12 to 20 carbon atoms, especially 17 to 19 carbon atoms.

Whilst the R group can be interrupted by at least one heteroatom or group of heteroatoms, this is not preferred and the R group backbone preferably contains only carbon atoms.

The R group may carry up to three substituents, e.g. selected from halo, $C_{1-6}$ alkyl e.g. methyl, or $C_{1-6}$ alkoxy. If present, the substituents are preferably non-polar, and small, e.g. a methyl group. It is preferred however, if the R group remains unsubstituted.

The R group is preferably an alkylene group.

The R group is preferably linear. It preferably derives from a natural source such as a long chain fatty acid or ester. In particular, the R group may derive from AA, EPA or DHA.

Thus, viewed from another aspect the invention employs a compound of formula (I')

R-L-CO—X  (I')

wherein R is a $C_{10\text{-}24}$ unsubstituted unsaturated alkylene group said group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof.

Ideally R is linear. R is therefore preferably an unsaturated $C_{10\text{-}24}$ polyalkylene chain.

The linking group L provides a bridging group of 1 to 5 backbone atoms, preferably 2 to 4 backbone atoms between the R group and the carbonyl, such as 2 atoms. The atoms in the backbone of the linker may be carbon and/or be heteroatoms such as N, O, S, SO, $SO_2$. The atoms should not form part of a ring and the backbone atoms of the linking group can be substituted with side chains, e.g. with groups such as $C_{1-6}$ alkyl, oxo, alkoxy, or halo.

Preferred components of the linking group are —$CH_2$—, —$CH(C_{1\text{-}6}alkyl)$-, —$N(C_{1\text{-}6}alkyl)$-, —NH—, —S—, —O—, —CH═CH—, —CO—, —SO—, —$SO_2$— which can be combined with each other in any (chemically meaningful) order to form the linking group. Thus, by using two methylene groups and an —S— group the linker —$SCH_2CH_2$— is formed. It will be appreciated that at least one component of the linker provides a heteroatom in the backbone.

The linking group L contains at least one heteroatom in the backbone. It is also preferred if the first backbone atom of the linking group attached to the R group is a heteroatom or group of heteroatoms.

It is highly preferred if the linking group L contains at least one —$CH_2$— link in the backbone. Ideally the atoms of the linking group adjacent the carbonyl are —$CH_2$—.

It is preferred that the group R or the group L (depending on the size of the L group) provides a heteroatom or group of heteroatoms positioned α, β, γ, or δ to the carbonyl, preferably β or γ to the carbonyl. Preferably the heteroatom is O, N or S or a sulphur derivative such as SO.

Highly preferred linking groups L therefore are —$NH_2CH_2$, —$NH(Me)CH_2$—, —$SCH_2$—, —$SOCH_2$—, or —$COCH_2$—

The linking group should not comprise a ring.

Highly preferred linking groups L are $SCH_2$, $NHCH_2$, and $N(Me)CH_2$.

Viewed from another aspect the invention employs a compound of formula (II)

R-L-CO—X  (II)

wherein R is a linear $C_{10\text{-}24}$ unsubstituted unsaturated alkylene group said group comprising at least 4 non-conjugated double bonds;

L is —$SCH_2$—, —$OCH_2$—, —$SOCH_2$, or —$SO_2CH_2$—; and

X is an electron withdrawing group or a salt thereof.

The group X is an electron withdrawing group. Suitable groups in this regard include O—$C_{1-6}$ alkyl, CN, $OCO_2$—$C_{1-6}$ alkyl, phenyl, $CHal_3$, $CHal_2H$, $CHalH_2$ wherein Hal represents a halogen, e. g. fluorine, chlorine, bromine or iodine, preferably fluorine.

In a preferred embodiment the electron withdrawing group is $CHal_3$, especially $CF_3$.

Thus, preferred compounds of formula (I) are those of formula (III)

R—Y1-Y2-CO—X  (III)

wherein R and X are as hereinbefore defined;

Y1 is selected from O, S, NH, $N(C_{1-6}$-alkyl), SO or $SO_2$ and

Y2 is $(CH)_n$ or $CH(C_{1-6}$ alkyl); or where n is 1 to 3, preferably 1.

More, preferred compounds of formula (I) are those of formula (IV)

wherein R is a linear $C_{10-24}$ unsubstituted unsaturated alkylene group said group comprising at least 4 non-conjugated double bonds;
X is as hereinbefore defined (e.g. $CF_3$); and
Y1 is selected from O, S, SO or $SO_2$.

Highly preferred compounds for use in the invention are depicted below.

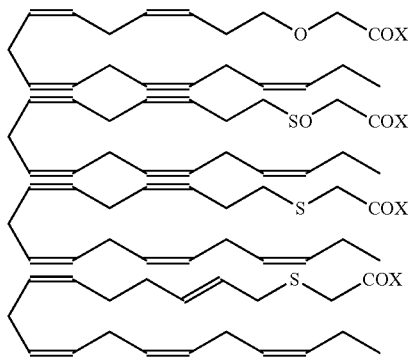

where X is as hereinbefore defined such as $CF_3$.

The following compounds are highly preferred for use in the invention:

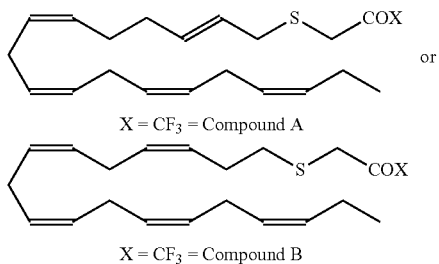

The second component of the composition or product of the invention is a compound of formula (X) as hereinbefore defined. In compounds of formula (X) it is preferred if $R_1$ is phenyl wherein said phenyl is substituted by lower alkyl substituted by cyano.

It is preferred if $R_3$ is methyl. It is preferred if $R_4$ is unsubstituted quinolinyl. It is preferred if the quinoline group $R_4$ binds via its N containing ring, especially via its 3-position.

The compound of formula (X) is preferably of formula (XI)

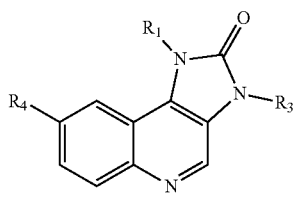

where $R_1$ is phenyl wherein said phenyl is substituted by lower alkyl unsubstituted or substituted by cyano;
$R_3$ is methyl; and
$R_4$ is quinolinyl unsubstituted or substituted by halogen;
or a salt thereof.

It is especially preferred if the compound (X) is 2-Methyl-[4-(3-methyl-2-oxo-8-quinolin-3-yl-2,3-dihydro-imidazo[4,5-c]quinolin-1-yl)-phenyl-propionitrile or a salt thereof such as toluene sulphonic acid salt thereof, i.e. the compound:

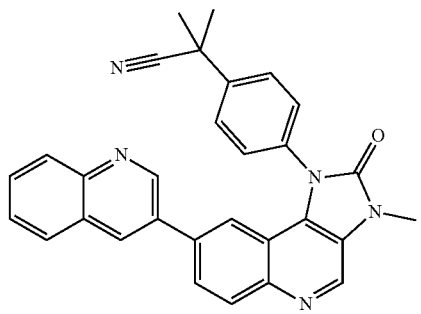 [SMILES: Cn1c(=O)n(-c2ccc(C(C)(C)C#N)cc2)c2c3cc(-c4cnc5ccccc5c4)ccc3ncc21]

or a salt thereof such as toluene sulphonic acid salt thereof. This compound is called BEZ235.

In a most preferred embodiment therefore the invention relates to a composition or combination product comprising Compound A or Compound B and BEZ235. Alternatively, another combination product of the invention is BEZ235, Compound A and Compound B.

Where possible, the compounds of the invention can be administered in salt, hydrate or solvate form, especially salt form.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (X) and the resulting mixture evaporated to dryness (lyophilised) to obtain the acid addition salt as a solid. Alternatively, a compound of formula (X) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (e.g. methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Compounds of formula (I) may be manufactured using known chemical synthetic routes. It is convenient to begin synthesis from the commercially available compounds arachidonic acid (AA), EPA (all-Z-eicosa-5,8,11,14,17-pentaenoic acid) or DHA (all-Z-docosa-4,7,10,13,16,19-hexaenoic acid). Conversion of the acid functionality of these compounds into, for example a —$COCF_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as $BrCH_2COCF_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

Synthesis methods for the preparation of compounds of formula (X) are described in EP-A-1888578, for example. Additional methods for assaying the activity of PI3K inhibitors, mTOR inhibitors and dual PI3K/mTOR inhibitors have been described. See WO2015/04939 and US Pat. Publication 2014/0066474, and Brana et al. (2012) *BMC Med.* 10:161, for example. The weight ratio of the compounds of formula (I) to compounds of formula (X) in composition or combination product of the invention will be guided by intended use, and the age and general health of the subject, and other parameters known to those of skill. For example, a particular weight ratio suitable for certain applications may be 10 to 90 wt % to 90 to 10 wt %, such as 30 to 70 wt % to 70 to 30 wt %.

More preferably, the amounts of each compound are determined in molar terms, and the ratio of each is 5:1 to 1:5 moles, such as 2:1 to 1:2 moles. Often, the compounds are used in an equimolar amount for certain applications The amount of the compounds of the invention in the composition will often be determined by the physician depending on the dosage required.

The composition or combination product of the invention is proposed primarily for use in the treatment or prevention of proliferative disorders such as cancer.

By treating or treatment is meant at least one of:
(i). inhibiting the disease i.e. arresting, reducing or delaying the development of the disease or a relapse thereof or at least one clinical or subclinical symptom thereof, or
(ii). relieving or attenuating one or more of the clinical or subclinical symptoms of the disease.

By prevention is meant (i) preventing or delaying the appearance of clinical symptoms of the disease developing in a mammal.

The benefit to a subject to be treated is either statistically significant or at least perceptible to the patient or to the physician. In general a skilled man can appreciate when "treatment" occurs. It is particularly preferred if the composition or combination product of the invention are used therapeutically, i.e. to treat a condition which has manifested rather than prophylactically. It may be that the composition or combination product of the invention is more effective when used therapeutically than prophylactically.

The composition or combination product of the invention can be used on any animal subject, in particular a mammal and more particularly to a human or an animal serving as a model for a disease (e.g., mouse, monkey, etc.).

In order to treat a disease an effective amount of the active composition or combination product needs to be administered to a patient. A "therapeutically effective amount" means the amount of a composition or combination product that, when administered to an animal for treating a state, disorder or condition, is sufficient to effect such treatment. The "therapeutically effective amount" will vary depending on the composition or combination product, the disease and its severity and the age, weight, physical condition and responsiveness of the subject to be treated and will be ultimately at the discretion of the attendant doctor.

It may be that to treat cancer according to the invention that the composition or combination product of the invention has to be readministered at certain intervals. Suitable dosage regimes can be prescribed by a physician.

The composition or combination product of the invention typically comprises the active components in admixture with at least one pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of cancer.

It will be appreciated that pharmaceutical composition or combination products for use in accordance with the present invention may be in the form of oral, parenteral, transdermal, sublingual, topical, implant, nasal, or enterally administered (or other mucosally administered) suspensions, capsules or tablets, which may be formulated in conventional manner using one or more pharmaceutically acceptable carriers or excipients. The compositions of the invention could also be formulated as nanoparticle formulations.

However, for the treatment of cancer, the composition or combination product of the invention will preferably be administered orally or by parenteral or intravenous administration, such as injection. The composition or combination product may therefore be provided in the form of an tablet or solution for injection.

The pharmaceutical composition or combination product of the invention may contain from 0.01 to 99% weight—per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the present invention to administer the combination products described herein to a subject that has been exposed to, is being exposed to, or will be exposed to one or more anti-proliferative compounds and particularly those known to be used in many anti-cancer therapies. Non-limiting examples include aromatase inhibitors, anti-estrogens, topoisomerase I or II inhibitors microtubule active compounds, alkylating compounds, histone deacetylase inhibitors, and cyclooxygenase inhibitors such as those disclosed in WO2006/122806 and references cited therein Choice of whether to combine a combination product of the invention with one or more of the aforementioned anti-cancer therapies will be guided by recognized parameters known to those of skill in the field, including the particular type of cancer being treated, the age and health of the subject, etc.

The invention is described further below with reference to the following non-limiting examples and FIGURES.

DESCRIPTION OF FIGURES

FIG. 1 shows co-treatment with cPLA2α inhibitor Compound B and BEZ235 shows synergistic effects on breast cancer cell viability compared to each inhibitor alone. Average and standard deviation of 4 experiments performed in 8 wells.

EXAMPLES

The following compounds were used in the Experiments:

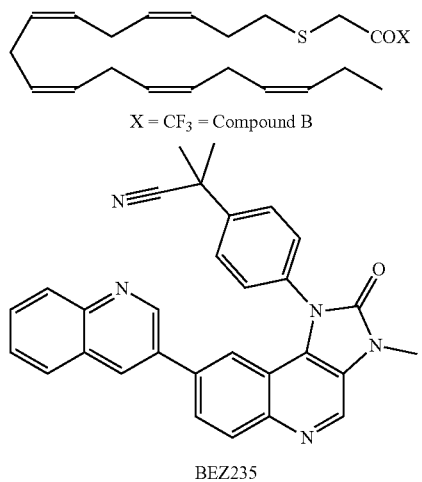

Methods

Cell Culture. The MDA-MB-468 cell line was from ATCC. This cell line was established from a pleural effusion of patient with metastatic breast adenocarcinoma. The cells were maintained in RPMI medium supplemented with 10% (v/v) FBS, 0.3 mg/mL L-glutamine, and 0.1 mg/mL gentamicin at 37° C. in 5% CO2. Sub-culture using trypsin-EDTA was performed every 3-4 days with a split ratio of 1:3-1:6 to ensure actively proliferating cells.

Resazurin Viability Assay. Cells were seeded in fully supplemented medium at a density of 7 000 cells per well in 96 well plates. After 24 hrs of cultivation, when the cells were ~60% confluent, the medium was replaced with serum free medium to ensure synchronization of the cells and to increase cell sensitivity to treatment. Following 16 hrs of serum starvation, the medium was replaced with fresh serum free medium with or without Compound B, (Avexxin, Norway), and NVP-BEZ235 (Cayman Chemicals, US) or solvent (DMSO, Sigma Aldrich, US). The cells were observed under the microscope to evaluate possible morphology changes and signs of stress before the addition of resazurin according to the manufacturers instructions (RnD Systems, UK). Resazurin was metabolized for 2 hrs (37° C., 5% CO2) before fluorescence was read at 544 nm excitation and 590 nm emission wavelengths (BioTek Synergy HT).

Results

Co-treatment with the cPLA2α inhibitor Compound B and the PI3K/mTOR inhibitor NVP-BEZ235 shows synergistic effects on breast cancer cell viability compared to each inhibitor alone. Initial experiments were performed to determine the effects of each inhibitor alone. Both Compound B and BEZ235 were toxic to the cells at 25-100 μM, whereas at doses 1-5 μM, little or no signs of cellular stress of cytotoxicity were observed (results not shown). On this basis, combination treatment experiments were designed in which sub-toxic doses of the inhibitors were combined. Following 24 hrs of treatment, 5 μM BEZ235 and Compound B modestly reduced viability by ~30% and 20%, respectively. However, when the two inhibitors at 5 μM were combined, a 70% reduction of viability was found, indicating a synergistic and beneficial effect on cancer cell proliferation (FIG. 1). Statistically, our results show: ¤ p<0.005 vs. Ctrl and #p<0.0005 vs. single treatment.

What is claimed is:

1. A combination product comprising:

(A) Compound A or Compound B represented by one of the formulas below:

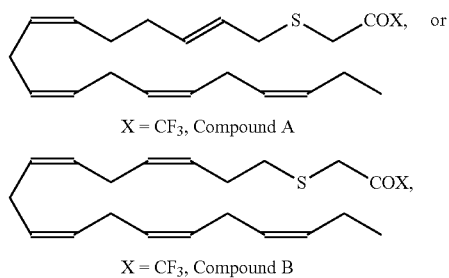

or a salt thereof; and (B) Compound BEZ235 represented by the formula below:

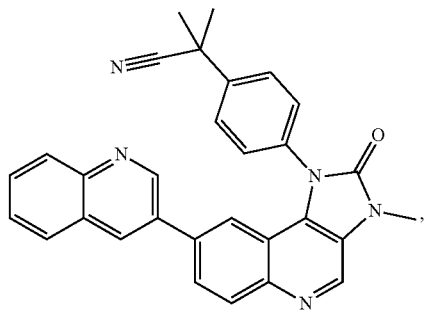 [SMILES: Cn1c(=O)n(-c2ccc(C(C)(C)C#N)cc2)c2c3cc(-c4cnc5ccccc5c4)ccc3ncc21]

or a pharmaceutically acceptable salt thereof.

2. A pharmaceutical composition comprising:
(A) Compound A or Compound B represented by one of the formulas below:

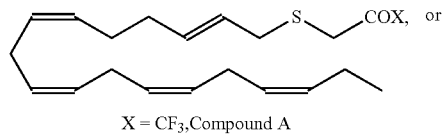

X = CF₃, Compound A

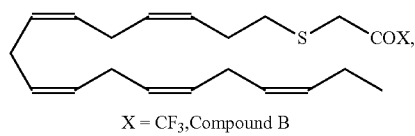

X = CF₃, Compound B or a salt thereof; and
(B) Compound BEZ235 represented by the formula below:

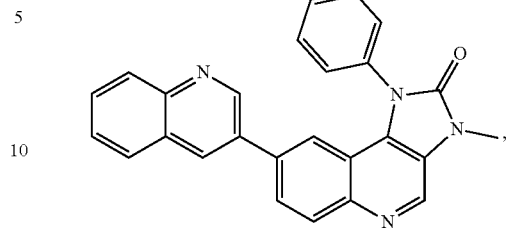

or a pharmaceutically acceptable salt thereof; and a pharmaceutically acceptable diluent or carrier.

3. The pharmaceutical composition of claim 2 wherein the pharmaceutical composition is a fixed combination or non-fixed combination.

4. The combination product of claim 1, wherein the combination product is a fixed combination or non-fixed combination.

5. The combination product of claim 1, wherein the pharmaceutically acceptable salt of Compound BEZ235 is a 4-toluenesulfonic acid salt thereof.

6. The pharmaceutical composition of claim 2, wherein the pharmaceutically acceptable salt of Compound BEZ235 is a 4-toluenesulfonic acid salt thereof.

* * * * *